(12) United States Patent
Bozzano et al.

(10) Patent No.: US 7,586,018 B2
(45) Date of Patent: Sep. 8, 2009

(54) OXYGENATE CONVERSION TO OLEFINS WITH DIMERIZATION AND METATHESIS

(75) Inventors: Andrea G. Bozzano, Northbrook, IL (US); Bryan K. Glover, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 13 days.

(21) Appl. No.: 11/643,604

(22) Filed: Dec. 21, 2006

(65) Prior Publication Data

US 2008/0154078 A1 Jun. 26, 2008

(51) Int. Cl.
*C07C 1/207* (2006.01)
*C07C 6/04* (2006.01)

(52) U.S. Cl. .................. 585/317; 585/329; 585/638; 585/643

(58) Field of Classification Search .................. 585/327, 585/329, 638, 643
See application file for complete search history.

(56) References Cited

U.S. PATENT DOCUMENTS

| | | | |
|---|---|---|---|
| 3,876,599 A | 4/1975 | Attridge et al. | |
| 4,049,741 A | 9/1977 | Kuo et al. | |
| 4,231,947 A | 11/1980 | Schrock | |
| 4,245,131 A | 1/1981 | Schrock | |
| 4,409,409 A | 10/1983 | Langer, Jr. et al. | |
| 4,962,267 A | 10/1990 | Slaugh | |
| 5,990,369 A * | 11/1999 | Barger et al. | 548/640 |
| 6,005,150 A | 12/1999 | Vora | |
| 6,049,017 A | 4/2000 | Vora et al. | |
| 6,156,947 A | 12/2000 | Vora | |
| 6,211,423 B1 | 4/2001 | Slaugh et al. | |
| 6,225,359 B1 | 5/2001 | O'Rear et al. | |
| 6,271,434 B1 | 8/2001 | Slaugh et al. | |
| 2003/0233018 A1 | 12/2003 | Brown et al. | |

OTHER PUBLICATIONS

Hydrocarbon Processing; Mar. 2003; XP-002322126.*

* cited by examiner

*Primary Examiner*—Thuan Dinh Dang
(74) *Attorney, Agent, or Firm*—James C Paschall; Mark Goldberg

(57) ABSTRACT

A processing scheme and system for enhanced light olefin production, particularly for increased relative yield of propylene, involves oxygenate conversion to olefins and subsequent oxygenate conversion effluent stream treatment including dimerization of ethylene to butene and metathesis of butenes and/or hexenes with ethylene. The processing scheme and system may further involve isomerization of at least a portion of 1-butene to 2-butene to produce additional propylene.

7 Claims, 4 Drawing Sheets

OXYGENATE CONVERSION TO OLEFINS WITH DIMERIZATION AND METATHESIS

FIELD OF THE INVENTION

This invention relates generally to the conversion of oxygenates to olefins and, more particularly, to light olefins.

BACKGROUND OF THE INVENTION

A major portion of the worldwide petrochemical industry is in involved with the production of light olefin materials and their subsequent use in the production of numerous important chemical products via polymerization, oligomerization, alkylation and the like well-known chemical reactions. Light olefins include ethylene, propylene and combinations thereof. These light olefins are essential building blocks for the modern petrochemical and chemical industries. The major source for these materials in present day refining is the stream cracking of petroleum feeds. For various reasons including geographical, economic, political and diminished supply considerations, the art has long sought a source other than petroleum for the massive quantities of raw materials that are needed to supply the demand for these light olefin materials.

The search for alternative materials for light olefin production has led to the use of oxygenates such as alcohols and, more particularly, to the use of methanol, ethanol, and higher alcohols or their derivatives such as dimethyl ether, diethyl ether, etc., for example. Molecular sieves such as microporous crystalline zeolite and non-zeolite catalysts, particularly silicoaluminophosphates (SAPO), are known to promote the conversion of oxygenates to hydrocarbon mixtures, particularly hydrocarbon mixtures composed largely of light olefins.

Such processing of oxygenates to form light olefins is commonly referred to as a methanol-to-olefin (MTO) process, as methanol alone or together with other oxygenate materials such as dimethyl ether (DME) is typically an oxygenate material most commonly employed therein. In practice, such oxygenate conversion processing arrangements commonly produce ethylene and propylene as main products and, as stand alone processing, can achieve propylene to ethylene product ratios up to about 1.4. In addition to the production of ethylene and propylene as main products, such processing also typically produces or results in smaller relative amounts of highly olefinic $C_4$ and heavier hydrocarbon streams.

Commonly assigned U.S. Pat. No. 5,990,369 to Barger et al. discloses a process for the production of light olefins comprising olefins having from 2 to 4 carbon atoms per molecule from oxygenate feedstock. The process comprises passing the oxygenate feedstock to an oxygenate conversion zone containing a metal aluminophosphate catalyst to produce a light olefin stream. The light olefin stream is fractionated and a portion of the products are metathesized to enhance the yield of ethylene, propylene and/or butylene products. Propylene can be metathesized to produce an additional quantity of ethylene, or a combination of ethylene and butene can be metathesized to produce an additional quantity of propylene. The combination of light olefin production and metathesis or disproportionation is disclosed as providing flexibility such as to overcome the equilibrium limitations of the metal aluminophosphate catalyst in the oxygenate conversion zone. In addition, the invention thereof is disclosed as providing the advantage of extended catalyst life and greater catalyst stability in the oxygenate conversion zone.

While such processing can desirably result in the formation of increased relative amounts of propylene, further improvements such as to further enhance the relative amount of propylene production and recovery are desired and have been sought.

SUMMARY OF THE INVENTION

A general object of the invention is to provide or result in improved processing of an oxygenate-containing feedstock to light olefins.

A more specific objective of the invention is to overcome one or more of the problems described above.

The general object of the invention can be attained, at least in part, through a specified process for producing light olefins from an oxygenate-containing feedstock. In accordance with one embodiment, such a process involves contacting the oxygenate-containing feedstock in an oxygenate conversion reactor with an oxygenate conversion catalyst and at reaction conditions effective to convert the oxygenate-containing feedstock to form an oxygenate conversion effluent stream comprising light olefins and $C_4+$ hydrocarbons, wherein the light olefins comprise ethylene and the $C_4+$ hydrocarbons comprise a quantity of butenes. The oxygenate conversion stream is treated in a separation zone and forms a first process stream comprising at least a portion of the ethylene from the oxygenate conversion effluent stream. At least a portion of the ethylene from the first process stream is dimerized in a dimerization zone to produce a dimerized stream comprising quantity of butenes. At least a portion of the butenes from the dimerized stream is contacted with ethylene in a metathesis zone at effective conditions to produce a metathesis effluent stream comprising propylene, with at least a portion of this propylene desirably recovered therefrom. The process can further include forming in the separation zone a second process stream comprising at least a portion of the quantity of butenes including a quantity of 1-butenes from the oxygenate conversion effluent stream and contacting at least a portion of the quantity of butenes from the second process stream with ethylene in the metathesis zone to produce propylene.

The prior art generally fails to provide processing schemes and arrangements for the conversion of an oxygenate-containing feedstock to olefins that maximizes production of propylene to as great an extent as may be desired. Moreover, the prior art generally fails to provide a processing scheme and arrangement as effective and efficient as may be desired in increasing the relative yield of propylene in association with the conversion of oxygenate materials to light olefins.

A process for producing light olefins from an oxygenate-containing feedstock in accordance with another embodiment involves contacting an oxygenate-containing feedstock in an oxygenate conversion reactor with an oxygenate conversion catalyst and at reaction conditions effective to convert the oxygenate-containing feedstock to form an oxygenate conversion effluent stream comprising light olefins and $C_4+$ hydrocarbons, wherein the light olefins comprise a quantity of ethylene and the $C_4+$ hydrocarbons comprises a quantity of diolefins and a quantity of butenes including a quantity of 1-butenes. The oxygenate conversion effluent stream is separated in a separation zone and forms a first process stream comprising at least a portion of the quantity of ethylene from the oxygenate conversion effluent stream. At least a portion of the quantity of ethylene from the first process stream is dimerized in a dimerization zone to produce a dimerized stream comprising a residual quantity of ethylene, a quantity of butenes including a quantity of 1-butenes, and a quantity of hexenes. At least a portion of the quantity of residual ethylene from the dimerized stream is metathesized with at least a portion of the quantity of hexenes from the dimerized stream in first metathesis zone to produce a first metathesis effluent stream comprising a quantity of butenes including a quantity of 1-butenes and a quantity of propylene. At least a portion of the quantity of 1-butenes from the first metathesis effluent stream is isomerized in an isomerization zone to produce an isomerized stream comprising a quantity of 2-butenes. At least a portion of the 2-butenes from the isomerized stream is metathesized with ethylene in a second metathesis zone to produce a second metathesis effluent stream comprising propylene. Propylene can then be appropriately recovered from the second metathesis effluent stream. The process can additionally include forming in the separation zone a second process stream comprising at least a portion of the quantity of diolefins and at least a portion of the quantity of butenes, including a quantity of 1-butenes, from the oxygenate conversion effluent stream and metathesizing at least a portion of the quantity of butenes from the second process stream with ethylene in the second metathesis zone to produce propylene. The process can further include hydrogenating at least a portion of the diolefins from the second process stream in a hydrogenation zone to produce a hydrogenation effluent stream comprising an additional quantity of 1-butenes and isomerizing at least a portion of the quantity of 1-butenes from the hydrogenation effluent stream in the isomerization zone to produce an additional quantity of 2-butenes.

There is also provided a system for producing light olefins from an oxygenate-containing feedstock. In accordance with one embodiment, such a system includes a reactor for contacting an oxygenate-containing feedstream with an oxygenate conversion catalyst and converting the oxygenate-containing feedstream to an oxygenate conversion effluent stream comprising light olefins and $C_4+$ hydrocarbons, wherein the light olefins comprise a quantity of ethylene and the $C_4+$ hydrocarbons comprise a quantity of butenes. A separation zone is provided for separating the oxygenate conversion effluent stream and forming a first process stream comprising at least a portion of the quantity of ethylene from the oxygenate conversion effluent stream. A dimerization zone is provided for dimerizing at least a portion of the quantity of ethylene from the first process stream to produce a dimerized stream comprising a quantity of butenes, including a quantity of 1-butenes, and a quantity of hexenes. The system also includes a metathesis zone for contacting at least a portion of the butenes from the dimerized stream with ethylene to produce a metathesis effluent stream comprising propylene. A recovery zone is also provided for recovering propylene from the metathesis effluent stream.

As used herein, references to "light olefins" are to be understood to generally refer to $C_2$ and $C_3$ olefins, i.e., ethylene and propylene, alone or in combination.

References to "$C_x$ hydrocarbon" are to be understood to refer to hydrocarbon molecules having the number of carbon atoms represented by the subscript "x". Similarly, the term "$C_x$-containing stream" refers to a stream that contains $C_x$ hydrocarbon. The term "$C_x+$ hydrocarbons" refers to hydrocarbon molecules having the number of carbon atoms represented by the subscript "x" or greater. For example, "$C_4+$ hydrocarbons" include $C_4$, $C_5$ and higher carbon number hydrocarbons. The term "$C_x-$ hydrocarbons" refers to hydrocarbon molecules having the number of carbon atoms represented by the subscript "x" or fewer. For example, "$C_4-$ hydrocarbons" include $C_4$, $C_3$ and lower carbon number hydrocarbons.

Other objects and advantages will be apparent to those skilled in the art from the following detailed description taken in conjunction with the appended claims and drawings.

Those skilled in the art and guided by the teachings herein provided will recognize and appreciate that the illustrated systems or process flow diagrams have been simplified by the elimination of various usual or customary pieces of process equipment including some heat exchangers, process control systems, pumps, fractionation systems, and the like. It may also be discerned that the process flow diagrams depicted in the figures may be modified in many aspects without departing from the basic overall concept of the invention.

DETAILED DESCRIPTION

Oxygenate-containing feedstocks can be converted to light olefins in a catalytic reactor and heavier hydrocarbons (e.g., $C_4+$ hydrocarbons) formed during such processing can be subsequently treated such that at least a portion of the quantity of ethylene formed upon such conversion is subsequently dimerized to form a stream containing at least butenes. Such butenes can then be metathesized to produce additional propylene.

Figure 1:
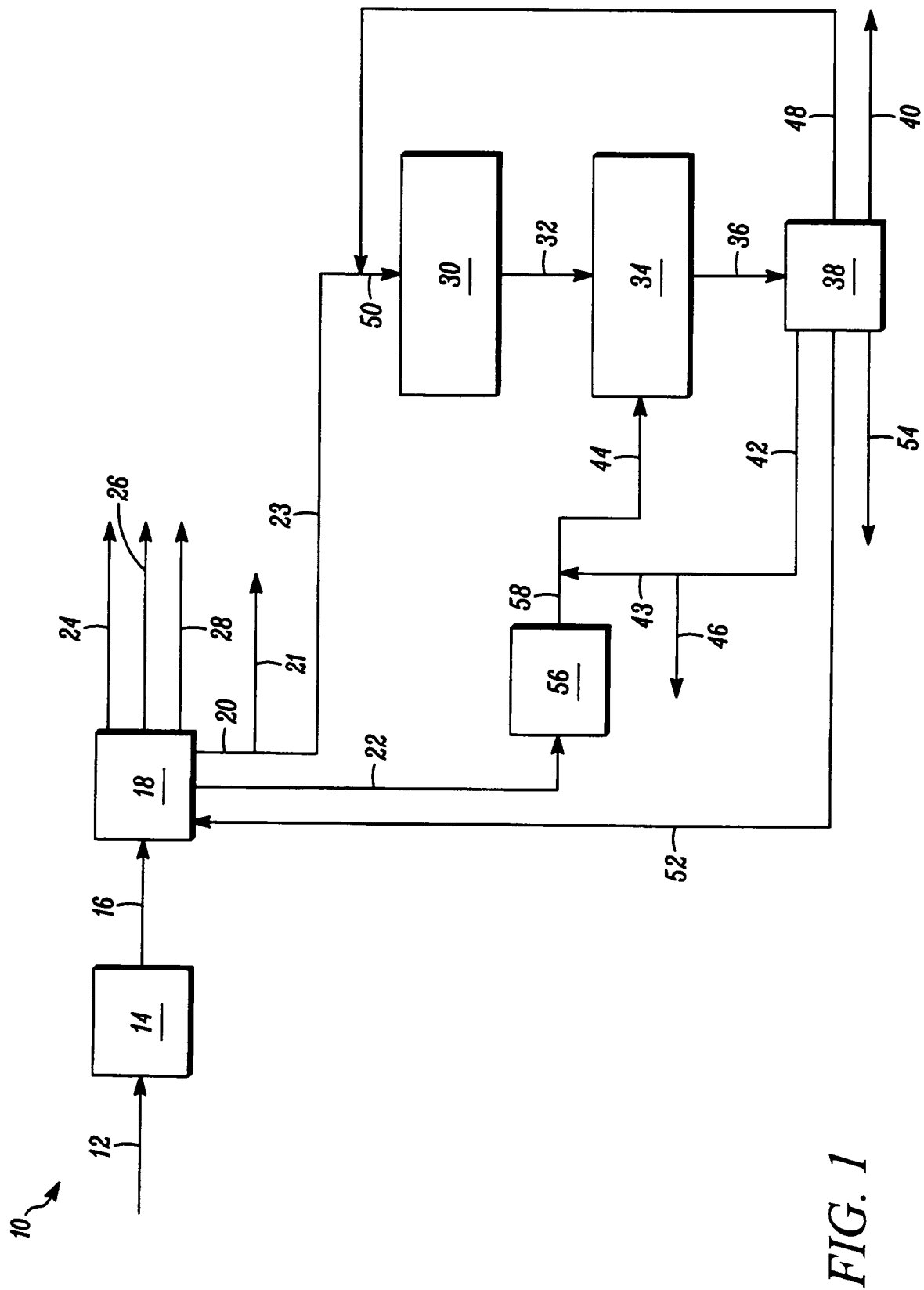
FIG. 1 is a simplified schematic process flow diagram illustrating a process for the conversion of oxygenates to olefins employing a dimerization zone, to enhance the relative amount of butenes, and a metathesis zone, to enhance the relative yield of propylene, in accordance with one embodiment.

As will be appreciated such processing may be embodied in a variety of processing arrangements. As representative, FIG. 1 illustrates a simplified schematic process flow diagram for a processing scheme, generally designated with the reference numeral 10, for the conversion of oxygenates to olefins and employing a dimerization zone and a metathesis zone to enhance the yield of propylene, in accordance with one embodiment.

More particularly, an oxygenate-containing feedstock or feedstream in such is generally composed of light oxygenates such as one or more of methanol, ethanol, dimethyl ether, diethyl ether, or combinations thereof, is introduced via a line 12 into an oxygenate conversion zone or reactor section 14 wherein the oxygenate-containing feedstock contacts with an oxygenate conversion catalyst at reaction conditions effective to convert the oxygenate-containing feedstock to form an oxygenate conversion effluent stream in a line 16 comprising fuel gas hydrocarbons, light olefins, and $C_4+$ hydrocarbons, in a manner as is known in the art, such as, for example, utilizing a fluidized bed reactor.

As will be appreciated by those skilled in the art and guided by the teachings herein provided, such a feedstock may be commercial grade methanol, crude methanol or any methanol purity therebetween. Crude methanol may be an unrefined product from a methanol synthesis unit. Those skilled in the art and guided by the teachings herein provided will understand and appreciate that in the interest of factors such as improved catalyst stability, embodiments utilizing higher purity methanol feed may be preferred. Thus, suitable feeds in such embodiments may comprise methanol or a methanol and water blend, with possible such feeds having a methanol content of between about 65% and about 100% by weight, preferably a methanol content of between about 80% and about 100% by weight and, in accordance certain embodiments, a methanol content of between about 95% and about 100% by weight.

A methanol-to-olefin unit feedstream may comprise between about 0 wt. % and about 35 wt. % and more preferably about 5 wt. % and about 30 wt. % water. The methanol in the feedstream may comprise between about 70 wt. % and about 100 wt. % and more preferably between about 75 wt. % and about 95 wt. % of the feedstream. The ethanol in the feedstream may comprise between about 0.01 wt. % and about 0.5 wt. % and more typically between about 0.1 wt. % and about 0.2 wt. % of the feedstream although higher concentrations may be beneficial. When methanol is the primary component in the feedstream, the higher alcohols in the feedstream may comprise between about 200 wppm and about 2000 wppm and more typically about between about 500 wppm and 1500 wppm. Additionally, when methanol is the primary component in the feedstream, dimethyl ether may comprise between about 100 wppm and about 20,000 wppm and more typically between about 200 wppm and about 10000 wppm.

The invention, however, also contemplates and encompasses embodiments wherein the oxygenate-containing feedstock includes dimethyl ether, either alone or in combination with water, methanol or in combination with both water and methanol, for example. The invention specifically encompasses embodiments wherein the oxygenate-containing feedstock is essentially dimethyl ether either alone or with no more than insubstantial amounts of other oxygenate materials.

Reaction conditions for the conversion of oxygenate to light olefins are known to those skilled in the art. Preferably, in accordance with particular embodiments, reaction conditions comprise a temperature between about 200° C. and about 700° C., more preferably between about 300° C. and about 600° C., and most preferably between about 400° C. and about 550° C. In addition, reactor operating pressures typically are preferably superatmospheric and such as generally range from about 69 kPa gauge to about 689 kPa gauge (about 10 psig to about 100 psig), as may be required to accommodate sufficient pressure at the compressor section.

As will be appreciated by those skilled in the art and guided by the teachings herein provided, the reaction conditions are generally variable such as dependent on the desired products. For example, if increased ethylene production is desired, then operation at a reactor temperature between about 475° C. and about 550° C. and more preferably between about 500° C. and about 520° C., may be preferred. If increased propylene production is desired, then operation at a reactor temperature between about 350° C. and about 475° C. and more preferably between about 400° C. and about 430° C. may be preferred. In addition, higher pressures tend to yield slightly more propylene relative to ethylene.

The light olefins produced can have a ratio of ethylene to propylene of between about 0.5 and about 2.0 and preferably between about 0.75 to about 1.25. If a higher ratio of ethylene to propylene is desired, then the reaction temperature is generally desirably higher than if a lower ratio of ethylene to propylene is desired. In accordance with one embodiment, a feed temperature of between about 120° C. and about 210° C. is preferred. In accordance with another embodiment, a feed temperature of between about 180° C. and about 210° C. is preferred. In accordance with a further embodiment, the temperature is desirably maintained below 210° C. to avoid or minimize thermal decomposition.

The oxygenate conversion zone 14 produces or results in the formation of an oxygenate conversion effluent stream in the line 16 such as generally comprising fuel gas hydrocarbons, light olefins, and $C_4+$ hydrocarbons. The light olefins comprise a quantity of ethylene and the $C_4+$ hydrocarbons generally typically comprise a quantity of diolefins as well as a quantity of butenes including a quantity of 1-butenes.

The oxygenate conversion effluent stream, or at least a portion thereof, is passed via the line 16 to an oxygenate conversion effluent stream treatment or separation of zone, generally designated by reference numeral 18, wherein the oxygenate conversion effluent stream is resolved, e.g., fractionated, using conventional separation means, to form a first process stream in a line 20 comprising at least a portion of the quantity of ethylene from the oxygenate conversion effluent stream. Such conventional separation means are described in greater detail below in conjunction with, for example, FIG. 2.

The oxygenate conversion effluent stream in the line 16 may be further resolved, e.g., fractionated, using conventional separation means, to form a second process stream in a line 22 comprising at least a portion of the quantity of diolefins and at least a portion of the quantity of butenes, including a portion of the quantity of 1-butenes, from the oxygenate conversion effluent stream. Such conventional separation means are described in greater detail below in conjunction with, for example, FIG. 2. Other process streams that may be separated from the oxygenate conversion effluent stream the line 16 in the treatment or separation zone 18 include, for example, a propylene product stream 24, a paraffins stream 26 comprising, for example, propane, and a stream 28 of heavy hydrocarbons generally typically comprising $C_5+$ hydrocarbons.

The first process stream, or at least a portion thereof, is passed via lines 20, 23 and 50 to a dimerization zone 30 wherein at least a portion of the quantity of ethylene from the first product stream is dimerized over a dimerization catalyst and at reaction conditions effective to result in or produce a dimerized stream in a line 32 comprising a quantity of butenes. In accordance with certain embodiments, a drag stream 21 may be provided to reduce the build-up of selected undesirable hydrocarbon components such as, for example, ethane, in the dimerization zone 30.

The dimerization reaction can generally be carried out under conditions and employ catalysts such as are known in the art. For example, such dimerization catalysts may be homogeneous or heterogeneous, with the heterogeneous catalysts typically being preferred. The dimerization catalyst may preferably comprise a catalytically effective amount of a transition metal component. Preferred transition metals for use in the practice of the present invention include tungsten, molybdenum, nickel, rhenium, and combinations thereof, with nickel being preferred. The transition metal component may be present as elemental metal and/or one or more compounds of the metal. If the catalyst is heterogeneous, it is preferred that the transition metal component be associated with a support. Any suitable support material may be employed provided that it does not substantially interfere with the feedstock components. Preferably, the support material comprises silica, silica-alumina, Y-zeolite, X-zeolite, a polymeric material, sulfated alumina, and ZSM-5. Silica-alumina is a particularly preferred support material. If a support material is employed, the amount of transition metal component used in combination with the support material may vary widely, depending, for example, on the particular application involved and/or the transition metal being used.

Typical or usual dimerization reaction conditions, such as when employing a nickel on silica-alumina catalyst, may involve a temperature of about 80° C. to about 120° C. and typically a pressure of about 3 MPa (about 435 psia). Lower temperatures are generally, typically preferred to promote dimerization of ethylene to butenes and pentenes and to limit or prevent skeletal isomerization of the butenes to other olefin products.

Desirably, the extent of the dimerization reaction can be controlled such as by controlling the temperature and/or pressure within the dimerization zone 30 and/or by controlling the amount of ethylene from the first process stream in line 20 which bypasses the dimerization zone 30 (i.e., via the drag stream 21) so as to control the ethylene to butene ratio in the dimerized stream in the line 32. In accordance with one embodiment, operating conditions in the dimerization zone 30 are controlled to maintain an ethylene to butene ratio of about 1:1 to about 5:1 and a butene selectivity in the dimerized stream of at least about 80%, and preferably at least about 90%.

The dimerized stream, or at least a portion thereof, is introduced via the line 32 into a metathesis zone 34 and under effective conditions wherein at least a portion of the butenes from the dimerized stream is contacted with ethylene to produce a metathesis effluent stream in a line 36 comprising propylene. In accordance with certain embodiments, the metathesis effluent stream can additionally include a residual quantity of ethylene, a residual quantity of butenes, a quantity of $C_5$ and/or $C_6$ hydrocarbons such as generally composed of pentenes and hexenes, and a quantity of heavy hydrocarbon materials generally composed of materials heavier than hexane.

The metathesis reaction can generally be carried out under conditions and employ catalysts such as are known in the art. In accordance with one embodiment, a metathesis catalyst such as containing a catalytic amount of at least one of molybdenum oxide and tungsten oxide is suitable for the metathesis reaction. Conditions for the metathesis reaction in the vapor phase generally include a reaction temperature ranging from about 20° C. to about 450° C., preferably 250° C. to 350° C., and pressures varying from about atmospheric to upwards of 20.6 MPa gauge (3000 psig), preferably between about 3000 kPa gauge to 3500 kPa gauge (435 psig to 510 psig), although higher pressures can be employed if desired. Conditions for the metathesis reaction in the liquid phase generally include a reaction temperature ranging from about 25° C. to 50° C. and pressures sufficient to maintain a liquid phase. Catalysts which are active for the metathesis of olefins and which can be used in the process of this invention are of a generally known type. In this regard, reference is made to "Journal of Catalysis", 13 (1969) pages 99-114, to "Applied Catalysis", 10 (1984) pages 29-229 and to "Catalysis Review", 3 (1) (1969) pages 37-60.

Such metathesis catalysts may be homogeneous or heterogeneous, with the heterogeneous catalysts being preferred. The metathesis catalyst preferably comprises a catalytically effective amount of transition metal component. Preferred transition metals for use in the present invention include tungsten, molybdenum, nickel, rhenium, and combinations thereof. The transition metal component may be present as elemental metal and/or one or more compounds of the metal. If the catalyst is heterogeneous, it is generally preferred that the transition metal component be associated with a support. Any suitable support material may be employed provided that it does not substantially interfere with the feedstock components or the lower olefin component conversion. Preferably, the support material is an oxide, such as silica, alumina, titania, zirconia, and combinations thereof. Silica is a particularly preferred support material. If a support material is employed, the amount of transition metal component used in combination with the support material may vary widely, depending, for example, on the particular application involved and/or the transition metal being used. Preferably, the transition metal comprises about 1% to about 20%, by weight (calculated as elemental metal) of the total catalyst. The metathesis catalyst advantageously comprises a catalytically effective amount of at least one of the above-noted transition metals, and is capable of promoting olefin metathesis. The catalyst may also contain at least one activating agent present in an amount to improve the effectiveness of the catalyst. Various activating agents may be employed, including activating agents which are well known in the art to facilitate metathesis reactions. Light olefins metathesis catalysts can, for example, desirably be complexes of tungsten (W), molybdenum (Mo), or rhenium (Re) in a heterogeneous or homogeneous phase.

The metathesis effluent stream, or at least a portion thereof, is introduced via the line 36 into a metathesis fractionation zone 38 wherein the metathesis effluent stream is resolved, e.g., fractionated, by conventional separation means into a propylene product stream 40 and a butenes fraction in a line 42 generally composed of at least a portion of the residual quantity of butenes from the metathesis effluent stream. The butenes fraction (i.e., a butenes recycle stream), or at least a portion thereof, can be recycled back into the processing scheme 10 such as, for example, by introducing the butenes fraction in the line 42 into the metathesis zone 34 via lines 43 and 44. In embodiments wherein such butenes fraction from the metathesis fractionation zone 38 is recycled to the metathesis zone 34, a drag or purge stream 46 may be provided to reduce the build-up of selected hydrocarbon components such as, for example, isobutene, in the process loop.

The metathesis effluent stream in the line 36, or at least a portion thereof, can be further treated in the metathesis fractionation zone 38 to produce or result in the formation of an ethylene recycle stream in a line 48 generally composed of at least a portion of the residual quantity of ethylene from the metathesis effluent stream in the line 36 and which can be subsequently recycled to the dimerization zone 30. In practice, at least a portion of the ethylene recycle stream in the line 48 can be combined with the first process stream in the line 20 and such combined stream can be introduced into the dimerization zone 30 via the line 50.

The metathesis effluent stream in the line 36 can be further resolved, e.g., fractionated, in the metathesis fractionation zone 38, such as by conventional distillation methods, to produce a third stream generally composed of at least a portion of the $C_5$ and/or $C_6$ hydrocarbons which can be introduced into the oxygenate conversion effluent treatment zone 18 via a line 52 for further processing. Alternatively, the third process stream can be removed from the processing scheme 10. For example, the third process stream, or a portion thereof, can be used as fuel.

The metathesis effluent stream in the line 36 can be further resolved, e.g., fractionated, in the metathesis fractionation zone 38, such as by conventional distillation methods, to produce a heavy hydrocarbon purge stream 54. In practice, the heavy hydrocarbon purge stream 54, or a portion thereof, can be used as fuel. For example, for locations in proximity to refineries, such materials or select portions thereof can be blended into a gasoline pool. Additionally or alternatively, depending upon the specifications as to the olefin content in a feed to a synthesis gas unit, the heavy hydrocarbon purge stream 54 or a portion thereof can be recycled to a front-end synthesis gas unit.

In accordance with certain embodiments, at least a portion of the butenes including a portion of the quantity of 1-butenes from the second process stream in the line 22 can be contacted with ethylene in the metathesis zone 34 to produce an additional quantity of propylene. Additionally or alternatively, the processing scheme 10 can include a hydrogenation zone 56 wherein at least a portion of the quantity of diolefins from the second process stream in the line 22 can be hydrogenated to produce a hydrogenation effluent stream in a line 58 comprising an additional quantity of 1-butenes. In practice, at least a portion of the hydrogenation effluent stream in the line 58, alone or in combination with at least a portion of the butenes recycle stream in the line 42, can be introduced into the metathesis zone 34 via the line 44 to produce an additional quantity of propylene.

Figure 2:
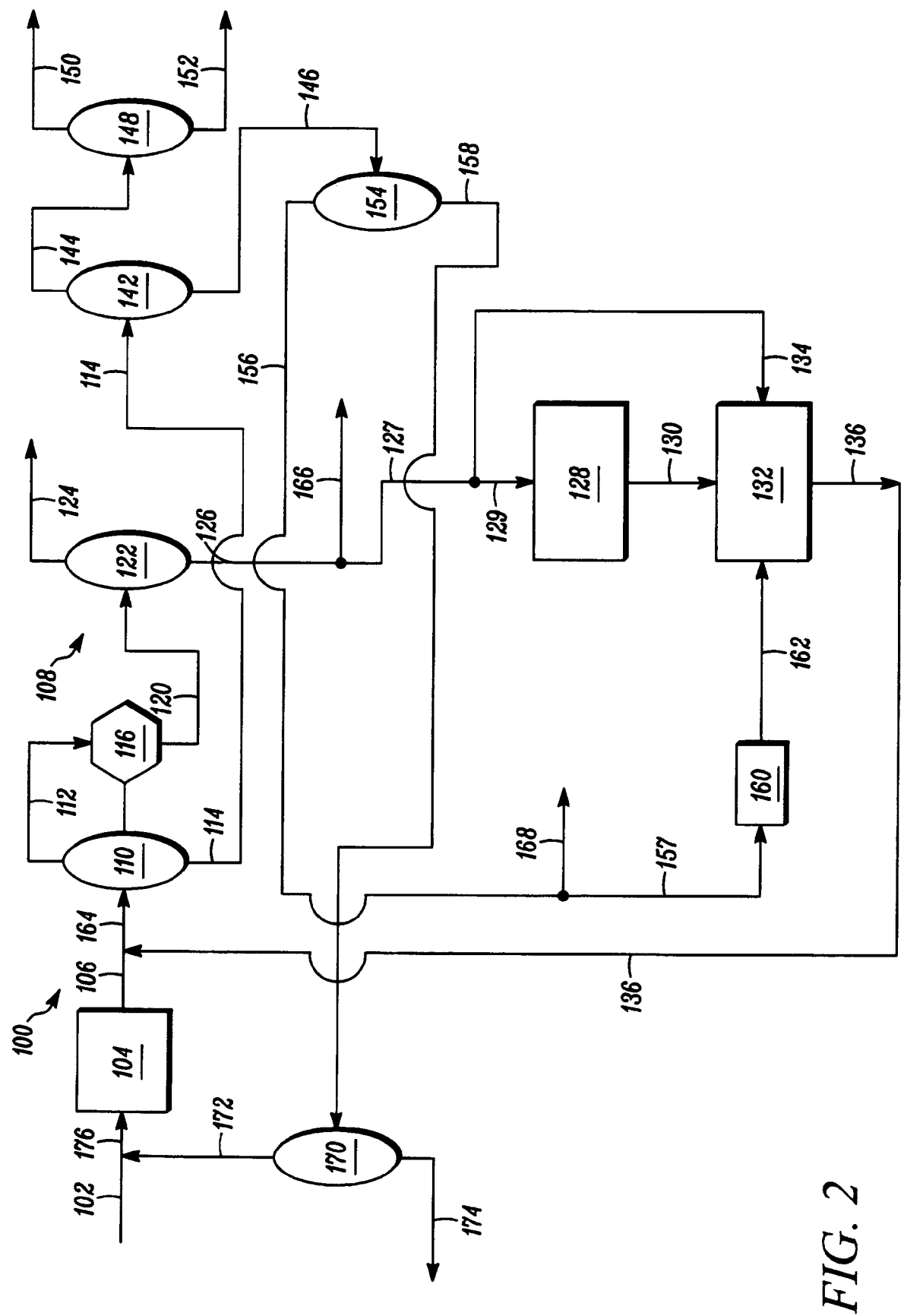
FIG. 2 is a simplified schematic process flow diagram illustrating a process for the conversion of oxygenates to olefins employing a dimerization zone, to enhance the relative amount of butenes, and a metathesis zone, to enhance the relative yield of propylene, in accordance with another embodiment.

In accordance with another embodiment, as illustrated in FIG. 2, a processing scheme 100 for producing light olefins from an oxygenate-containing feedstock involves introducing, via lines 102 and 176, an oxygenate-containing feedstock or feedstream such as generally composed of light oxygenates such as one or more of methanol, ethanol, dimethyl ether, diethyl ether, or combinations thereof, into an oxygenate conversion zone or reactor section 104 wherein the oxygenate-containing feedstock contacts with an oxygenate conversion catalyst at reaction conditions effective to convert the oxygenate-containing feedstock to form an oxygenate conversion effluent stream in a line 106 comprising fuel gas hydrocarbons, light olefins including ethylene, and $C_4+$ hydrocarbons including butenes and diolefins (e.g., butadienes), in a manner as is known in the art, such as, for example, utilizing a fluidized bed reactor.

The oxygenate conversion effluent stream in the line 106 can be further processed in a separation or treatment zone 108 wherein the oxygenate conversion effluent stream, or at least a portion thereof, may be separated or fractionated, such as by conventional distillation methods, to provide one or more process streams.

In accordance with certain embodiments, the oxygenate conversion effluent stream, or a select portion thereof, is passed via lines 106 and 164 to a deethanizer zone 110. In the deethanizer zone 110, the oxygenate conversion effluent stream is fractionated, such as by conventional distillation methods, such as to provide or form a deethanizer overhead stream in a line 112 comprising $C_2-$ hydrocarbons including methane, ethane, ethylene, acetylene and inert species such as $N_2$, CO, and the like, and a deethanized $C_3+$ bottoms stream in a line 114 comprising components heavier than ethane, such as propylene, propane, mixed butenes, diolefins (e.g., butadienes) and/or butane.

The deethanizer overhead stream, or at least a portion thereof, is passed via the line 112 to an acetylene saturation zone 116, wherein at least a portion of the acetylene from the deethanizer overhead stream is treated to produce a treated stream in a line 120 comprising an additional quantity of ethylene.

A demethanizer zone can generally typically be employed to avoid the undesired build-up of carbon dioxide in the processing scheme 100 and to prolong the life of dimerization and/or metathesis catalysts employed therein. In accordance with one embodiment, the treated stream, or at least a portion thereof, is passed via the line 120 to a demethanizer or $C_2$ fractionation zone 122 wherein the treated stream is fractionated, such as by conventional distillation methods, to form a demethanizer overhead stream in a line 124 comprising methane and inert species such as $N_2$, CO, and the like, if present, and a first process stream in a line 126 comprising $C_2$ materials including ethane and ethylene.

The first process stream, or at least a portion thereof, is passed via lines 126, 127 and 129 to a dimerization zone 128 wherein at least a portion of the ethylene from the first process stream is dimerized over a dimerization catalyst and at reaction conditions effective to result in or produce a dimerized stream in a line 130 comprising a quantity of butenes, a quantity of hexenes and a residual quantity of ethylene. The dimerization reaction can generally employ catalysts and can generally be carried out as described in detail above in conjunction with the dimerization zone 30, as illustrated in FIG. 1.

The dimerized stream, or at least a portion thereof, is passed via the line 130 to a metathesis zone 132 wherein at least a portion of the quantity of butenes and/or at least a portion of the quantity of hexenes from the dimerized stream is contacted with a quantity of ethylene over a metathesis catalyst to produce a metathesis effluent stream in a line 136 comprising propylene. The metathesis reaction can generally employ catalysts and be carried out as described in detail above in conjunction with the metathesis zone 34, as illustrated in FIG. 1.

In accordance with certain embodiments, at least a portion of the residual quantity of ethylene from the dimerized stream in the line 130 can provide a quantity of ethylene to support the metathesis reaction. In accordance with certain other embodiments, a portion of the first process stream in the line 126 can be introduced into the metathesis zone 132 via a line 134 to provide the quantity of ethylene for the metathesis reaction In accordance with certain embodiments, an additional quantity of butenes can be introduced into the metathesis zone 132 to produce an additional quantity of propylene. In practice, such additional quantity of butenes may be derived or formed, for example, from of the deethanized $C_3+$ bottoms stream in the line 114.

The deethanized $C_3+$ bottoms stream, or at least a portion thereof, can be passed via the line 114 to a depropanizer zone 142. In the depropanizer zone 142, the deethanized $C_3+$ bottoms stream in the line 114 is fractionated, such as by conventional distillation methods, to form a depropanizer overhead stream in a line 144 comprising $C_3$ materials including propylene and propane and a depropanized stream in a line 146 comprising $C_4+$ hydrocarbons comprising components heavier than propane, including a quantity of mixed butenes and a quantity of diolefins. The depropanizer overhead stream, or at least a portion thereof, can be passed via the line 144 to a $C_3$ splitter 148, wherein the depropanizer overhead stream is treated, e.g., fractionated, such as by conventional distillation methods, to provide an overhead propylene product stream 150 such as generally composed of propylene and a bottoms stream 152 such as generally composed of propane.

The depropanized stream, or at least a portion thereof, can be passed via the line 146 to a debutanizer or $C_4$ fractionation zone 154. In the debutanizer zone 154, the depropanized stream can be treated, e.g., fractionated, such as by conventional distillation methods, to form debutanizer overhead stream in a line 156 comprising $C_4$ materials including a quantity of mixed butenes and a quantity of diolefins (i.e., butadienes) and debutanized stream in a line 158 generally composed of materials heavier than butane.

In accordance with certain embodiments, at least a portion of the quantity of mixed butenes from the debutanizer overhead stream in the line 156 can be introduced directly into the metathesis zone 132. In accordance with certain other embodiments, the debutanizer overhead stream, or at least a portion thereof, is passed via lines 156 and 157 to a hydrogenation zone 160 wherein at least a portion of the quantity of diolefins from the debutanizer overhead stream are selectively hydrogenated to produce a hydrogenation effluent stream in a line 162 comprising an additional quantity of butenes. The additional quantity of butenes from the hydrogenation effluent stream, or at least a portion thereof, can be subsequently introduced into the metathesis zone 132 via the line 162 to produce an additional quantity of propylene via metathesis with ethylene.

Propylene is desirably recovered from the metathesis effluent stream in the line 136. In accordance with one embodiment, propylene is recovered by introducing the metathesis effluent stream, or a select portion thereof, via the line 136 into the separation zone 108. For example, the metathesis effluent stream in the line 136, or at least a portion thereof, can be combined with the oxygenate conversion effluent stream in the line 106 and such combined stream can be introduced into the separation section 108 via a line 164 wherein propylene is recovered from such combined stream according to the process described above in conjunction with the deethanizer zone 110, the depropanizer zone 142 and the $C_3$ splitter 148.

Alternatively, the metathesis effluent stream, or at least a portion thereof, can be passed via the line 136 to a metathesis fractionation zone (not shown) wherein the metathesis effluent stream is resolved, e.g., fractionated, by conventional separation means into a propylene product stream and a higher hydrocarbon fraction including butene which can be recycled back into the processing scheme 100 such as, for example, back into the any one of the deethanizer zone 110, the depropanizer zone 142, the debutanizer zone 154, or the metathesis zone 132. In embodiments wherein such higher hydrocarbon fraction from the metathesis fractionation zone is recycled to the metathesis zone 132, a drag stream can be provided to reduce the build-up of selected higher hydrocarbon components such as, for example, isobutene, in the process loop.

In accordance with certain embodiments, a drag stream 166 can be provided to reduce build-up of ethane in the processing scheme 100. The ethane-containing drag stream 166 can, for example, be disposed between the demethanizer zone 126 and the dimerization zone 128, i.e., drawn off from the first process stream in the line 126. The ethane-containing drag stream 166, or a portion thereof, can be recycled to a front-end synthesis gas unit or, if such unit is not readily available, can be used as fuel.

In accordance with certain embodiments, the processing scheme 100 can additionally include a $C_4$ purge stream 168 to avoid undesired build-up nonreacting materials (e.g., saturates) and, particularly, isobutenes, that might otherwise accumulate in the process loop. The $C_4$ purge stream 168 can be disposed between the debutanizer zone 154 and the metathesis zone 132, i.e., drawn off from the debutanizer overhead stream in the line 156.

In accordance with certain embodiments, the debutanized stream in the line 158, or at least a portion thereof, can be further treated, e.g., fractionated, such as by conventional distillation methods, in a heavy hydrocarbon separation zone 170. In the heavy hydrocarbon separation zone 170, the debutanized bottoms stream is treated to form an overhead stream in a line 172 generally composed of $C_5$ and/or $C_6$ hydrocarbons and a heavy hydrocarbon bottom stream 174 generally comprising components heavier than hexane. In practice the overhead stream, or a portion thereof, can be directly recycled to the oxygenate conversion zone 104 for further processing. Alternatively, at least a portion of the overhead stream in the line 172 can be combined with the oxygenate-containing feedstock and such combined stream can be introduced into the oxygenate conversion zone 104 via a line 176. In practice, the heavy hydrocarbon bottom stream 174, or a portion thereof, can be used as fuel. For example, for locations in proximity to refineries, such materials or select portions thereof can be blended into a gasoline pool. Additionally or alternatively, depending upon the specifications as to the olefin content in a feed to a synthesis gas unit, the heavy hydrocarbon bottoms stream 174, or a portion thereof, can be recycled to a front-end synthesis gas unit.

Figure 3:
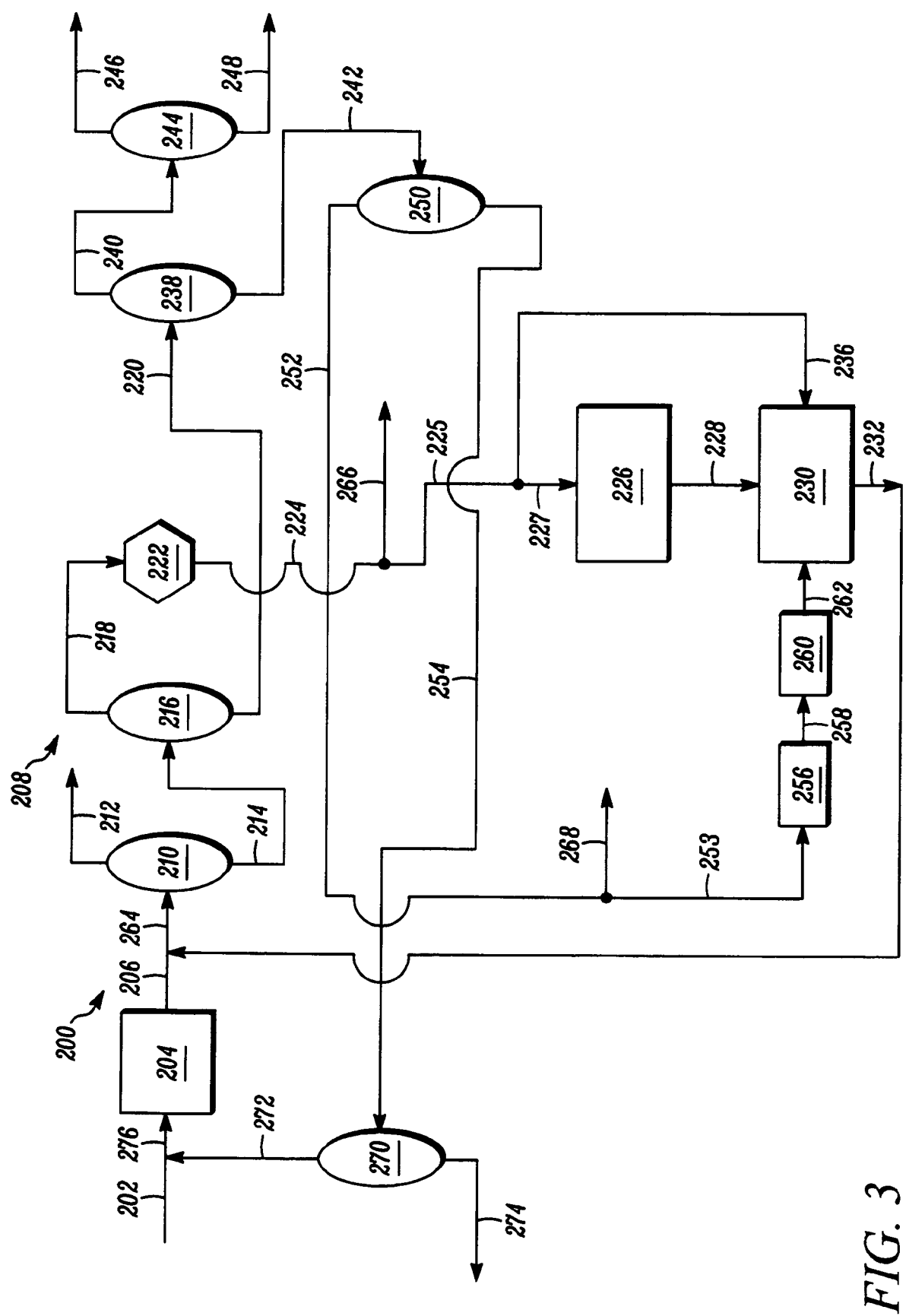
FIG. 3 is a simplified schematic process flow diagram illustrating a process for the conversion of oxygenates to olefins employing a dimerization zone, to enhance the relative amount of butenes, an isomerization zone, to enhance the relative amount of 2-butenes, and a metathesis zone, to enhance the relative yield of propylene, in accordance with a further embodiment.

In accordance with an additional embodiment, as illustrated in FIG. 3, a processing scheme 200 for producing light olefins from an oxygenate-containing feedstock involves introducing, via lines 202 and 276, an oxygenate-containing feedstock or feedstream such as generally composed of light oxygenates such as one or more of methanol, ethanol, dimethyl ether, diethyl ether, or combinations thereof, into an oxygenate conversion zone or reactor section 204 wherein the oxygenate-containing feedstock contacts with an oxygenate conversion catalyst at reaction conditions effective to convert the oxygenate-containing feedstock to form an oxygenate conversion effluent stream in a line 206 comprising fuel gas hydrocarbons, light olefins including ethylene, and $C_{4+}$ hydrocarbons including butenes and diolefins, in a manner as is known in the art, such as, for example, utilizing a fluidized bed reactor.

The oxygenate conversion effluent stream in the line 206 can be further processed in a separation or treatment zone 208 wherein the oxygenate conversion effluent stream, or at least a portion thereof, may be separated or fractionated, such as by conventional distillation methods, to provide one or more process streams.

In accordance with certain embodiments, the oxygenate conversion effluent stream, or a select portion thereof, is passed via lines 206 and 264 to a demethanizer zone 210. In the demethanizer zone 210, the oxygenate conversion effluent stream is fractionated, such as by conventional distillation methods, such as to provide or form a demethanizer overhead stream in a line 212 comprising methane and inert species such as $N_2$, CO, and the like, if present, and a demethanized $C_2$+ bottoms stream in a line 214 comprising components heavier than methane, such as ethylene, ethane, propylene, propane, mixed butenes, diolefins (e.g., butadienes) and/or butane. The demethanizer overhead stream in the line 212, or a portion thereof, can be used as fuel.

The demethanized $C_2$+ bottoms stream, or a select portion thereof, is passed via the line 214 to a deethanizer zone 216. In the deethanizer zone 216, the demethanized $C_2$+ bottoms stream is fractionated, such as by conventional distillation methods, such as to provide or form a deethanizer overhead stream in a line 218 comprising $C_2$ materials including ethane, ethylene, and possibly also some acetylene, and a deethanized $C_3+$ bottoms stream in a line 220 comprising components heavier than ethane, such as propylene, propane, mixed butenes, diolefins (e.g., butadienes) and/or butane.

The deethanizer overhead stream, or at least a portion thereof, is passed via the line 218 to an acetylene saturation zone 222, wherein at least a portion of the acetylene from the deethanizer overhead stream is treated to produce a first process stream in a line 224 comprising an additional quantity of ethylene.

The first process stream, or at least a portion thereof, is passed via lines 224, 225 and 227 to a dimerization zone 226 wherein at least a portion of the ethylene from the first process stream is dimerized over a dimerization catalyst and at reaction conditions effective to result in or produce a dimerized stream in a line 228 comprising a quantity of butenes, a quantity of hexenes and a residual quantity of ethylene. The dimerization reaction can generally employ catalysts and be carried out as described in detail above in conjunction with the dimerization zone 30, as illustrated in FIG. 1.

The dimerized stream, or at least a portion thereof, is passed via the line 228 to a metathesis zone 230 wherein at least a portion of the quantity of butenes and/or at least a portion of the quantity of hexenes from the dimerized stream is contacted with a quantity of ethylene over a metathesis catalyst to produce a metathesis effluent stream in a line 232 comprising propylene. The metathesis reaction can generally employ catalysts and be carried out as described in detail above in conjunction with the metathesis zone 34, as illustrated in FIG. 1.

In accordance with certain embodiments, at least a portion of the residual quantity of ethylene from the dimerized stream in the line 228 can provide the quantity of ethylene to support the metathesis reaction. In accordance with certain embodiments, a portion of the first process stream in the line 224 can be introduced into the metathesis zone 230 via a line 236 to provide the quantity of ethylene for the metathesis reaction In accordance with certain embodiments, an additional quantity of butenes can be introduced into the metathesis zone 230 to produce an additional quantity of propylene. In practice, such additional quantity of butenes may be derived or formed, for example, from of the deethanized $C_3+$ bottoms stream in the line 220.

The deethanized $C_3+$ bottoms stream, or at least a portion thereof, can be passed via the line 220 to a depropanizer zone 238. In the depropanizer zone 238, the deethanized $C_3+$ bottoms stream is fractionated, such as by conventional distillation methods, to form a depropanizer overhead stream in a line 240 comprising $C_3$ materials including propylene and propane and a depropanized stream in a line 242 comprising $C_4+$ hydrocarbons comprising components heavier than propane, including a quantity of mixed butenes and a quantity of diolefins. The depropanizer overhead stream, or at least a portion thereof, can be passed via the line 240 to a $C_3$ splitter 244, wherein the depropanizer overhead stream is treated, e.g., fractionated, such as by conventional distillation methods, to provide an overhead propylene product stream 246 such as generally composed of propylene and a bottoms stream 248 such as generally composed of propane.

The depropanized stream, or at least a portion thereof, can be passed via the line 242 to a debutanizer zone 250. In the debutanizer zone 250, the depropanized stream can be treated, e.g., fractionated, such as by conventional distillation methods, to form debutanizer overhead stream in a line 252 comprising $C_4$ materials including a quantity of 1-butenes, a quantity of 2-butenes, a quantity of isobutenes, and a quantity of diolefins (e.g., butadienes) and a debutanized stream in a line 254 generally composed of materials heavier than butane.

The debutanizer overhead stream, or at least a portion thereof, is passed via lines 252 and 253 to a hydrogenation zone 256 wherein at least a portion of the quantity of diolefins from the debutanizer overhead stream are selectively hydrogenated to produce a hydrogenation effluent stream in a line 258 comprising an additional quantity of butenes including a quantity of 1-butenes.

It has been found that the metathesis reaction of butenes with ethylene over a metathesis catalyst to produce propylene is favored where the butenes are in the form of 2-butenes rather than 1-butenes. Thus, in accordance with one embodiment, and as described in greater detail below, the hydrogenation effluent stream, or at least a portion thereof, is passed via the line 258 to an isomerization zone 260 for isomerizing at least a portion of the quantity of 1-butenes therein contained to form an isomerized stream in a line 262 comprising an increased quantity of 2-butenes.

As will be appreciated, such isomerization of 1-butenes to 2-butenes can desirably occur over a suitable isomerization catalyst at selected appropriate isomerization reaction conditions. In accordance with certain embodiments, the 1-butene to 2-butene isomerization reaction can be a hydroisomerization as it is generally conducted in the presence of a hydrogen atmosphere to facilitate the double bond migration, but such that the use of hydrogen is minimized to avoid undesirable hydrogenation side reactions. The catalysts typically employed in such processing are commonly based on noble metals (palladium, rhodium, platinum, etc.) deposited on an inert alumina support; palladium is normally preferred. Typical or usual reaction conditions may involve a temperature of about 100° C. to about 150° C. and typically a pressure of about 1.5 MPa to 2 MPa (about 215 psia to 300 psia). The feed to the hydroisomerization reactor is usually preheated by exchange with the reactor effluent and by steam. Such a heated feed then enters the reactor, which typically operates in a mixed phase with one or more catalyst beds. After cooling the isomerization products are typically flashed to remove excess hydrogen gas. The reaction temperature is generally chosen so as to maximize conversion to 2-butene (favored by lower temperatures) while still having a reasonable rate of reaction; hence it is commonly desirable to operate at a temperature of less than 150° C.

In accordance with certain other embodiments, the 1-butene to 2-butene isomerization reaction can be carried out in the absence of hydrogen. For example, the isomerization reaction can be carried out in the presence of a catalyst comprising ruthenium oxide and an alkali metal oxide base on an alumina or silica support. Typical or usual reaction conditions may involve a temperature of about 100° C. to about 200° C. and typically a pressure of up to about 6.9 MPa (about 1000 psig). When a flow of butenes is fed continuously over the catalyst, weight hourly space velocity (WHSV) can be in a range of from about 0.2 to about 10, and, typically, about 2 to about 4.

Desirably, the isomerized stream will contain 2-butene and 1-butene in a molar ratio of at least 8, e.g., at least 8 moles of 2-butenes per mole of 1-butenes, and, in accordance with at least certain embodiments, a molar ratio of greater than 10, e.g., more than 10 moles of 2-butene per mole of 1-butene. If fractionated, the residual 1-butene can be recycled to the isomerization reactor.

The isomerized stream, or at least a portion thereof, can be introduced via the line 262 into the metathesis zone 230 wherein the 2-butenes can be metathesized with ethylene to produce an additional quantity of propylene.

Propylene is desirably recovered from the metathesis effluent stream in the line 232. In accordance with one embodiment, propylene is recovered by introducing the metathesis effluent stream, or a select portion thereof, into the separation zone 208. For example, the metathesis effluent stream in the line 232, or at least a portion thereof, can be combined with the oxygenate conversion effluent stream in the line 206 and such combined stream can be introduced into the separation section 208 via a line 264 wherein propylene is recovered from such combined stream according to the process described above in conjunction with the demethanizer zone 210, the deethanizer zone 216, the depropanizer zone 238 and the $C_3$ splitter 244.

Alternatively, the metathesis effluent stream in the line 232, or at least a portion thereof, can be passed to a metathesis fractionation zone (not shown) wherein the metathesis effluent stream is resolved, e.g., fractionated, by conventional separation means into a propylene product stream and a higher hydrocarbon fraction including butene which can be recycled back into the processing scheme such as, for example, back into the any one of the demethanizer zone 210, the deethanizer zone 216, the depropanizer zone 238, the debutanizer zone 250, or the metathesis zone 230. In embodiments wherein such higher hydrocarbon fraction from the metathesis fractionation zone is recycled to the metathesis zone 230, a drag stream can be provided to reduce the build-up of selected higher hydrocarbon components such as, for example, isobutene, in the process loop.

In accordance with certain embodiments, a drag stream 266 can be provided to reduce build-up of ethane in the processing scheme 200. The ethane-containing drag stream 266 can, for example, be disposed between the acetylene saturation zone 222 and the dimerization zone 226, i.e., drawn off from the first process stream in the line 224. The ethane-containing drag stream 266, or a portion thereof, can be recycled to a front-end synthesis gas unit or, if such unit is not readily available, can be used as fuel.

In accordance with certain embodiments, the processing scheme 200 can additionally include a $C_4$ purge stream 268 to avoid undesired build-up nonreacting materials (e.g., saturates) and, particularly, isobutenes that might otherwise accumulate in the process loop. The $C_4$ purge stream 268 can be disposed between the debutanizer zone 250 and the hydrogenation zone 256, i.e., drawn off from the debutanizer overhead stream in the line 252.

In accordance with certain embodiments, the debutanized stream in the line 254, or at least a portion thereof, can be further treated, e.g., fractionated, such as by conventional distillation methods, in a heavy hydrocarbon separation zone 270. In the heavy hydrocarbon separation zone 270, the debutanized bottoms stream is treated to form an overhead stream in a line 272 generally composed of $C_5$ and/or $C_6$ hydrocarbons and a heavy hydrocarbon bottom stream 274 generally comprising components heavier than hexane. In practice the overhead stream, or a portion thereof, can be directly recycled to the oxygenate conversion zone 204 for further processing. Alternatively, at least apportion of the overhead stream in the line 272 can be combined with the oxygenate-containing feedstock in the line 202 and such combined stream can be introduced into the oxygenate conversion zone 204 via a line 276. In practice, the heavy hydrocarbon bottom stream 274, or a portion thereof, can be used as fuel. For example, for locations in proximity to refineries, such materials or select portions thereof can be blended into a gasoline pool. Additionally or alternatively, depending upon the specifications as to the olefin content in a feed to a synthesis gas unit, the heavy hydrocarbon bottoms stream 274, or a portion thereof, can be recycled to a front-end synthesis gas unit.

Figure 4:
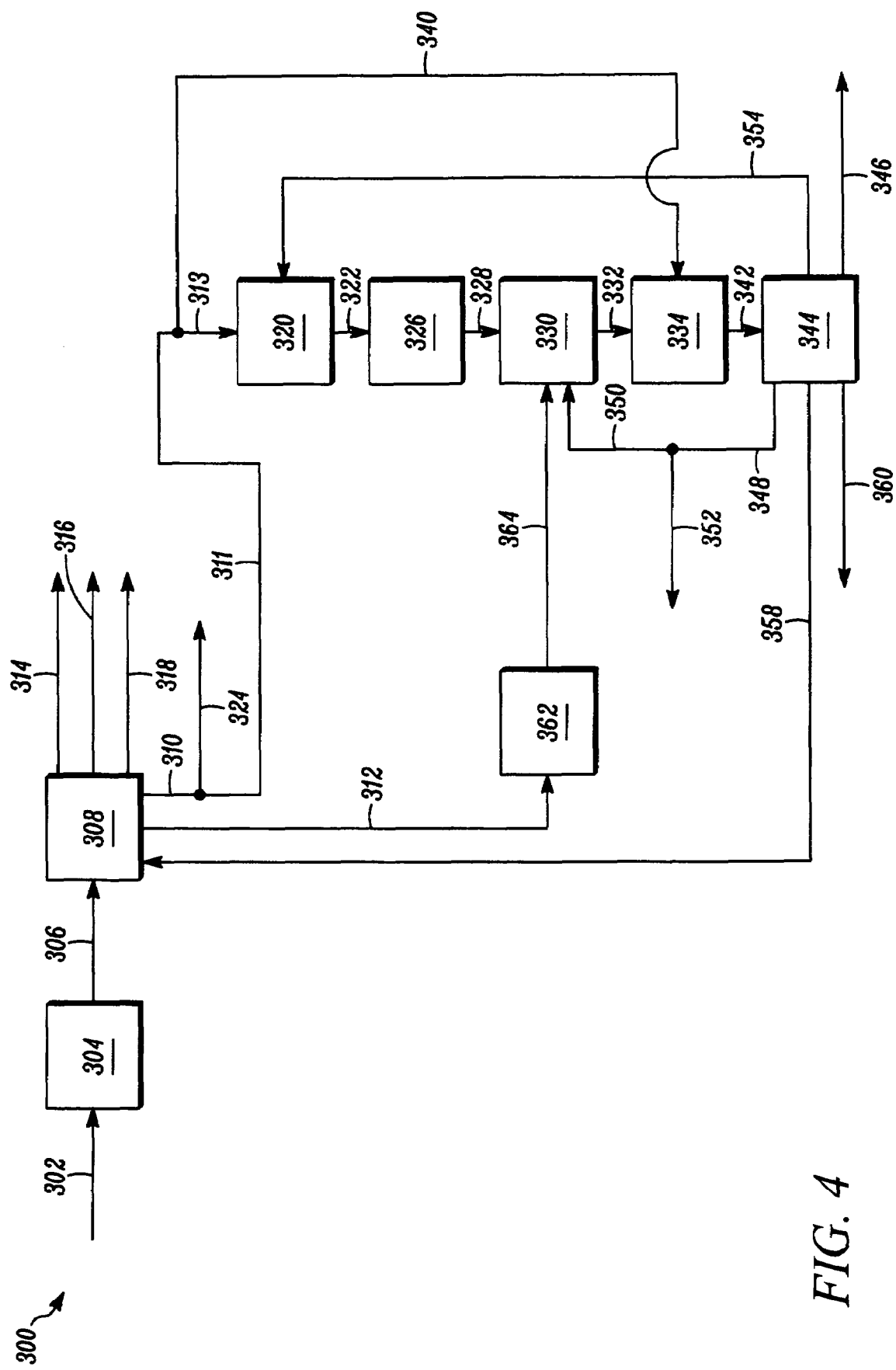
FIG. 4 is a simplified schematic process flow diagram illustrating a process for the conversion of oxygenates to olefins employing a dimerization zone, to enhance the relative amount of butenes, a first metathesis zone, to enhance the relative yield of propylene via metathesis of hexenes with ethylene, an isomerization zone, to enhance the relative amount of 2-butenes, and a second metathesis zone, to enhance the relative yield of propylene via metathesis of 2-butenes with ethylene, in accordance with an additional embodiment.

In accordance with a further embodiment, as illustrated in FIG. 4, a processing scheme 300 for producing olefins from an oxygenate-containing feedstock involves introducing, via a line 302, an oxygenate-containing feedstock or feedstream such as generally composed of light oxygenates such as one or more of methanol, ethanol, dimethyl ether, diethyl ether, or combinations thereof, into an oxygenate conversion zone or reactor section 304 wherein the oxygenate-containing feedstock contacts with an oxygenate conversion catalyst at reaction conditions effective to convert the oxygenate-containing feedstock to form an oxygenate conversion effluent stream in a line 306 comprising fuel gas hydrocarbons, light olefins, and $C_4+$ hydrocarbons, in a manner as is known in the art, such as, for example, utilizing a fluidized bed reactor. The light olefins comprise a quantity of ethylene and the $C_4+$ hydrocarbons generally typically comprise a quantity of diolefins as well as a quantity of butenes including a quantity of 1-butenes.

The oxygenate conversion effluent stream, or at least a portion thereof, is passed via the line 306 to an oxygenate conversion effluent stream treatment or separation zone 308, wherein the oxygenate conversion effluent stream is resolved, e.g., fractionated, by conventional separation means to form a first process stream in a line 310 comprising at least a portion of the quantity of ethylene from the oxygenate conversion effluent stream. Such conventional separation means are described in greater detail above in conjunction with, for example, FIG. 2 and FIG. 3.

The oxygenate conversion effluent stream in the line 306, or at least a portion thereof, may be further resolved, e.g., fractionated, by conventional separation means to form a second process stream in a line 312 comprising at least a portion of the quantity of diolefins and at least a portion of the quantity of butenes, including a portion of the quantity of 1-butenes, from the oxygenate conversion effluent stream. Other process streams that may be separated from the oxygenate conversion effluent stream in the line 306 in the treatment or separation zone 308 include, for example, a propylene product stream 314, a paraffins stream 316 comprising, for example, propane, and a heavy hydrocarbon stream 318 generally typically comprising $C_5+$ hydrocarbons.

The first process stream, or at least a portion thereof, is passed via lines 310, 311 and 313 to a dimerization zone 320 wherein at least a portion of the quantity of ethylene from the first product stream is dimerized over a dimerization catalyst and at reaction conditions effective to result in or produce a dimerized stream in a line 322 comprising a residual quantity of ethylene, a quantity of butenes, including a quantity of 1-butenes, and a quantity of hexenes. The dimerization reaction can generally employ catalysts and can generally be carried out as described in detail above in conjunction with the dimerization zone 30, as illustrated in FIG. 1.

In accordance with certain embodiments, a drag stream 324 may be provided to reduce the build-up of selected hydrocarbon components such as, for example, ethane in the dimerization zone 320.

The dimerized stream, or at least a portion thereof, is passed via the line 322 to a first metathesis zone or section 326. In the first metathesis zone 326, at least a portion of the residual quantity of ethylene from the dimerized stream is metathesized with at least a portion of the hexenes from the dimerized stream to produce a first or intermediate metathesis effluent stream in a line 328 comprising a quantity of butenes, including a quantity of 1-butenes, and a quantity of propylene. The first metathesis effluent stream in the line 328 can further comprise a quantity of pentenes.

The metathesis reaction in the first metathesis zone 326 can generally employ a catalyst such as described in detail above in conjunction with the metathesis zone 30, illustrated in FIG. 1. The metathesis reaction in the first metathesis zone 326 can generally be carried out at conditions effective to result in the conversion of at least a portion of the hexenes from the dimerized stream 328 to propylene. For example, the metathesis of hexene with ethylene can, for example, be carried out in the vapor phase at a temperature in a range of about 300° C. to about 350° C., and, typically, at about 330° C. The metathesis reaction can generally, typically carried out at a pressure of about 0.5 MPa (75 psia) with a WHSV of 50 to 100.

The first metathesis effluent stream, or at least a portion thereof, is passed via the line 328 to an isomerization zone 330. In the isomerization zone 330, at least a portion of the 1-butenes from the first metathesis effluent stream are isomerized to produce an isomerized stream in a line 332 comprising a quantity of 2-butenes. The isomerized stream in the line 332 can further include at least a portion of the quantity of pentenes and/or a portion of the quantity of propylene from the first metathesis effluent stream in the line 328. The isomerization reaction can generally employ catalysts and be carried out as described in detail above in conjunction with the isomerization zone 260, as illustrated in FIG. 3.

At least a portion of the quantity of 2-butenes from the isomerized stream and a quantity of ethylene, such as from a portion of the first process stream in the line 310, are introduced via lines 332 and 340, respectively, into a second metathesis zone or section 334 to produce a second metathesis effluent stream in a line 342 comprising propylene. In accordance with certain embodiments, at least a portion of the quantity of pentenes from the isomerized stream in the line 332 are also metathesized with ethylene in the second metathesis zone 334 to produce an additional quantity of propylene and a quantity of 1-butenes which can desirably be recovered from the second metathesis effluent stream.

The metathesis reaction can generally employ catalysts such as described in detail above in conjunction with the metathesis zone 34, as illustrated in FIG. 1. In accordance with certain embodiments, the metathesis of 2-butene with ethylene can, for example, be carried out in the vapor phase at about 300° C. to about 350° C. and about 0.5 MPa (75 psia) with a WHSV of 50 to 100 and a once-through conversion of about 15%, depending on the ethylene to 2-butene ratio.

The second metathesis effluent stream, or at least a portion thereof, is introduced via the line 342 into a metathesis fractionation zone 344 wherein the second metathesis effluent stream is resolved, e.g., fractionated, by conventional separation means into a propylene product stream 346 and a butenes fraction 348 generally composed of at least a portion of a residual quantity of butenes including, in accordance with certain embodiments, a portion of the quantity of 1-butenes from the second metathesis effluent stream. The butenes fraction 348, or at least a portion thereof, can be recycled back into the processing scheme 300 such as, for example, by introducing the butenes fraction 348 into the isomerization zone 330 via a line 350. In embodiments wherein such butenes fraction 348 from the metathesis fractionation zone 344 is recycled to the isomerization zone 330, a drag or purge stream 352 may be provided to reduce the build-up of select hydrocarbon components such as, for example, isobutene, in the process loop.

The second metathesis effluent stream in the line 342, or at least a portion thereof, can be further treated in the metathesis fractionation zone 344 to produce or result in the formation of an ethylene recycle stream in a line 354 generally composed of at least a portion of a residual quantity of ethylene from the second metathesis effluent stream and which can be subsequently recycled to the dimerization zone 320 via the line 354.

The second metathesis effluent stream in the line 342 can be further resolved in the metathesis fractionation zone 344, such as by conventional distillation methods, to produce a third process stream generally composed of $C_5$ and/or $C_6$ materials such as, for example, residual quantities of pentenes and/or hexenes from the second metathesis effluent stream, which can be introduced via a line 358 into the oxygenate conversion effluent treatment zone 308 for further processing. Alternatively, the third process stream can be removed from the processing scheme 300. For example, at least a portion of the third process stream can be used for fuel.

The second metathesis effluent stream in the line 342 can be further resolved, e.g., fractionated, in the metathesis fractionation zone 344, such as by conventional distillation methods, to produce a heavy hydrocarbon purge stream 360. In practice, the heavy hydrocarbon purge stream 360, or a portion thereof, can be used as fuel. For example, for locations in proximity to refineries, such materials or select portions thereof can be blended into a gasoline pool. Additionally or alternatively, depending upon the specifications as to the olefin content in a feed to a synthesis gas unit, the heavy hydrocarbon purge stream 360 or a portion thereof can be recycled to a front-end synthesis gas unit.

In accordance with certain embodiments, at least a portion of the butenes, including a quantity of 1-butenes, from the second process stream in the line 312 can be isomerized in the isomerization zone 330 to produce an additional quantity of 2-butenes. Additionally or alternatively, the processing scheme 300 can include a hydrogenation zone 362 wherein at least a portion of the quantity of diolefins from the second process stream in the line 312 can be hydrogenated to produce a hydrogenation effluent stream in a line 364 comprising an additional quantity of 1-butenes. In practice, the hydrogenation effluent stream, or at least a portion thereof, can be introduced into the isomerization zone 330 via the line 364 to produce an additional quantity of 2-butenes.

The invention illustratively disclosed herein suitably may be practiced in the absence of any element, part, step, component, or ingredient which is not specifically disclosed herein.

While in the foregoing detailed description this invention has been described in relation to certain embodiments thereof, and many details have been set forth for the purpose of illustration, it will be apparent to those skilled in the art that the invention is susceptible to additional embodiments and that certain of the details described herein can be varied considerably without departing from the basic principles of the invention.

The invention claimed is:

1. A process for producing light olefins from an oxygenate-containing feedstock, the process comprising:

contacting the oxygenate-containing feedstock in an oxygenate conversion reactor with an oxygenate conversion catalyst and at reaction conditions effective to convert the oxygenate-containing feedstock to an oxygenate conversion effluent stream comprising light olefins and $C_4+$ hydrocarbons, wherein the oxygenate-containing feedstock is selected from the group consisting of methanol, ethanol, dimethyl ether, diethyl ether, and combinations thereof, the light olefins comprise a quantity of ethylene and the $C_4+$ hydrocarbons comprise a quantity of diolefins and a quantity of butenes including a quantity of 1-butenes;

separating the oxygenate conversion effluent stream in a separation zone and forming a first process stream comprising at least a portion of the quantity of ethylene from the oxygenate conversion effluent stream;

dimerizing at least a portion of the quantity of ethylene from the first process stream in a dimerization zone to produce a dimerized stream comprising a residual quantity of ethylene, a quantity of butenes including a quantity of 1-butenes and a quantity hexenes;

metathesizing at least a portion of the residual quantity of ethylene from the dimerized steam with at least a portion of the quantity of hexenes from the dimerized stream in a first metathesis zone to produce a first metathesis effluent stream comprising a quantity of butenes including a quantity of 1-butenes, and a quantity of propylene;

isomerizing at least a portion of the quantity of 1-butenes from the first metathesis effluent stream in an isomerization zone to produce isomerized stream comprising a quantity of 2-butenes;

metathesizing at least a portion of the quantity of 2-butenes from the isomerized stream with ethylene in a second metathesis zone to produce a second metathesis effluent stream comprising propylene; and recovering propylene from the second metathesis effluent stream.

2. The process of claim 1 additionally comprising:
controlling operating conditions within the dimerization zone to maintain an ethylene to butene ratio in a range of about 1:1 to about 5:1 in the dimerized stream and a butene selectivity of at least about 80%.

3. The process of claim 1 additionally comprising:
forming a second process stream in the separation zone, the second process stream comprising at least a portion of the quantity of diolefins and at least a portion of the quantity of butenes, including a quantity of 1-butenes, from the oxygenate conversion effluent stream; and metathesizing at least a portion of the quantity of butenes from the second process stream with ethylene in the second metathesis zone to produce propylene.

4. The process of claim 3 additionally comprising:
hydrogenating at least a portion of the diolefins from the second process stream in a hydrogenation zone to produce a hydrogenation effluent stream comprising an additional quantity of 1-butenes; and isomerizing at least a portion of the quantity of 1-butenes from the hydrogenation effluent stream in the isomerization zone to produce an additional quantity of 2-butenes.

5. The process of claim 1 additionally comprising:
separating the second metathesis effluent stream in a fractionation zone to form a propylene product stream, an ethylene recycle stream, a butenes recycle stream and a third process stream comprising $C_5+$ hydrocarbons;

introducing at least a portion of the ethylene recycle stream into the dimerization zone;

introducing at least a portion of the butenes recycle stream into the isomerization zone; and introducing at least a portion of the third process stream into the separation zone.

6. The process of claim 1 additionally comprising:
recycling at least a portion of the second metathesis effluent stream to the separation zone.

7. The process of claim 1 additionally comprising:
introducing a portion of the of the quantity of ethylene from the first process stream into the second metathesis zone to metathesize with the 2-butenes from the isomerized stream to produce propylene.

* * * * *